US006959106B1

(12) United States Patent
Toth

(10) Patent No.: US 6,959,106 B1
(45) Date of Patent: Oct. 25, 2005

(54) METHOD AND APPARATUS FOR DETECTING LOW CONTRAST OBJECT IN A DIAGNOSTIC IMAGE

(75) Inventor: Thomas L. Toth, Brookfield, WI (US)

(73) Assignee: General Electric Company, Milwaukee, WI (US)

( * ) Notice: Subject to any disclaimer, the term of this patent is extended or adjusted under 35 U.S.C. 154(b) by 731 days.

(21) Appl. No.: 10/063,370

(22) Filed: Apr. 16, 2002

(51) Int. Cl.[7] .......................... G06K 9/00; G01D 18/00
(52) U.S. Cl. ...................... 382/128; 382/132; 378/207; 250/252.1
(58) Field of Search ............................... 382/128, 132, 382/100; 378/207; 702/85; 250/252.1

(56) References Cited

U.S. PATENT DOCUMENTS

| | | | | |
|---|---|---|---|---|
| 4,331,021 A | * | 5/1982 | Lopez et al. .................. | 73/1.86 |
| 5,414,479 A | * | 5/1995 | Ginsburg ...................... | 351/239 |
| 5,994,900 A | | 11/1999 | Gurvich ....................... | 324/300 |
| 6,694,047 B1 | * | 2/2004 | Farrokhnia et al. .......... | 382/132 |
| 2003/0020873 A1 | * | 1/2003 | Fink et al. ................... | 351/200 |
| 2003/0133076 A1 | * | 7/2003 | Lehmeier et al. ........... | 351/239 |

* cited by examiner

Primary Examiner—Jon Chang
Assistant Examiner—Anthony Mackowey
(74) Attorney, Agent, or Firm—Ziolkowski Patent Solutions Group, SC; Michael A. Della Penna; Carl B. Horton

(57) ABSTRACT

The present invention is directed to a method and apparatus of objectively testing the low contrast performance of an imaging system. Images of a uniform phantom and images of a low contrast detectability phantom are reconstructed. Thereafter, a group of pixels from an image of the uniform phantom are removed and replaced with a group of pixels from an image of the LCD phantom. A user or test observer is then prompted to identify which quadrant of the first phantom image contains a group of pixels from the LCD phantom. An accuracy of a user response is then determined and conveyed to the user. The present invention is applicable with a number of imaging modalities including computer tomography, magnetic resonance imaging, PET, ultrasound, and the like.

23 Claims, 3 Drawing Sheets

METHOD AND APPARATUS FOR DETECTING LOW CONTRAST OBJECT IN A DIAGNOSTIC IMAGE

BACKGROUND OF INVENTION

The present invention relates generally to diagnostic imaging and, more particularly, to a method and apparatus for testing the low contrast performance of a diagnostic imaging system.

The x-ray dose required by a CT imaging system to produce an image is becoming an increasingly important consideration to customers and regulatory agencies. The dose efficiency of a system is commonly tested using low contrast detectability (LCD) tests. Generally, images of phantoms are used to visually test the LCD performance of an imaging system. Phantoms can simulate anatomical regions of a subject such as the heart or lungs of a subject. Other phantoms may provide a simple set of low contrast hole patterns in a uniform background. A number of phantoms are available across diagnostic modalities.

Manufacturers generally specify low contrast detectability as the smallest size hole of a given contrast that can be visualized in a given phantom at or below a specified dose. Frequently when a new system is installed, tests are performed to demonstrate system performance. Additionally, periodic quality assurance tests are often performed to assure continued proper performance. These visual LCD specifications are often difficult to objectively measure because each observer must make a claim that a hole is present or not even though holes are always present in the phantom. As a result, there is often a large variability between observers. To improve objectivity, a number of methods have been proposed including what is commonly referred to as a Four Alternative Forced Choice (FAFC) test method. With this method, twelve scans are executed of a phantom having a low contrast object randomly placed in one of four quadrants of the phantom for each scan. A skilled observer then evaluates each image and determines which quadrant has the low contrast object. Generally, to pass the test it is necessary that the object be identified in at least nine of the twelve trials. The FAFC method is considered an objective test since the claims of the observer can be objectively scored as correct or incorrect. However, the low contrast object must be repositioned for each of the twelve scans to a random quadrant location unknown to the observer. Phantoms with a large variety of low contrast test objects that can be randomly positioned for an FAFC test can be expensive and are therefore not readily available. Furthermore, the FAFC method requires a minimum of two people, one who selects the random positions and another to perform the tasks of the observer who dose not know the true location of the low contrast object. The requirement for two thereby increases the expense of performing such tests.

Therefore, it would be desirable to design an apparatus and method of objective low contrast object detection that can be implemented with a single user/observer that is also cost effective.

BRIEF DESCRIPTION OF INVENTION

The present invention is a directed method and apparatus for testing the low contrast performance of an imaging system Images of a uniform phantom and images of a low contrast detectability phantom are reconstructed. Thereafter, a group of pixels from an image of the uniform phantom are removed and replaced with a group of pixels from an image of the LCD phantom. A user or test observer is then prompted to identify which quadrant of the first phantom image contains a group of pixels from the LCD phantom. An accuracy of a user response is then determined and conveyed to the user. The present invention is applicable with a number of imaging modalities including computer tomography, magnetic resonance imaging, PET, ultrasound, x-ray and the like.

In accordance with one aspect of the present invention, a method of testing for low contrast objects in a set of images is provided. The method includes the steps of positioning a first phantom and a second phantom in a scanning bay and acquiring imaging data of the phantoms. The method further includes the step of reconstructing a set of images for each of the phantoms from the imaging data wherein each image has a number of pixels. At least one pixel from an image of the first phantom is then interchanged with at least one pixel from an image of the second phantom and thereafter a user is prompted to identify the at least one pixel interchanged into the image of the first phantom.

In accordance with another aspect of the present invention, a computer readable storage medium having a computer program stored thereon for assisting a user in identifying a low contrast object in an image is provided. The computer program represents a set of instructions that when executed by a computer causes the computer to access an image of a uniform phantom as well as access an image of an LCD phantom. The set of instructions then causes the computer to randomly remove the set of pixels of the image of the uniform phantom and replace with a set of pixels of the image of the LCD phantom. A test image is then reconstructed therefrom. The computer is then caused to display the test image and prompt the user to identify the set of pixels from the image of the LCD phantom within the test image and then determine an accuracy of a user response identifying the set of pixels from the image of the LCD phantom within the test image.

In accordance with a further aspect of the present invention, a diagnostic imaging system includes an imaging bay and a table configured to position a subject to be imaged in the imaging bay. The imaging system further includes a DAS configured to acquire imaging data of the subject as well as a computer programmed to acquire imaging data of a uniform phantom and an LCD phantom. The computer is also programmed to reconstruct an image of the uniform phantom from the imaging data wherein the uniform phantom has a generally uniform noise intensity. The computer is also programmed to reconstruct an image of the phantoms from the imaging data. A portion of the image of the LCD phantom is then incorporated into the image of the uniform phantom to form a test image. The computer is then programmed to display the test image to a user and prompt the user to identify the portion of the test image containing the LCD object. A user response is then received and an accuracy of the user response is determined.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
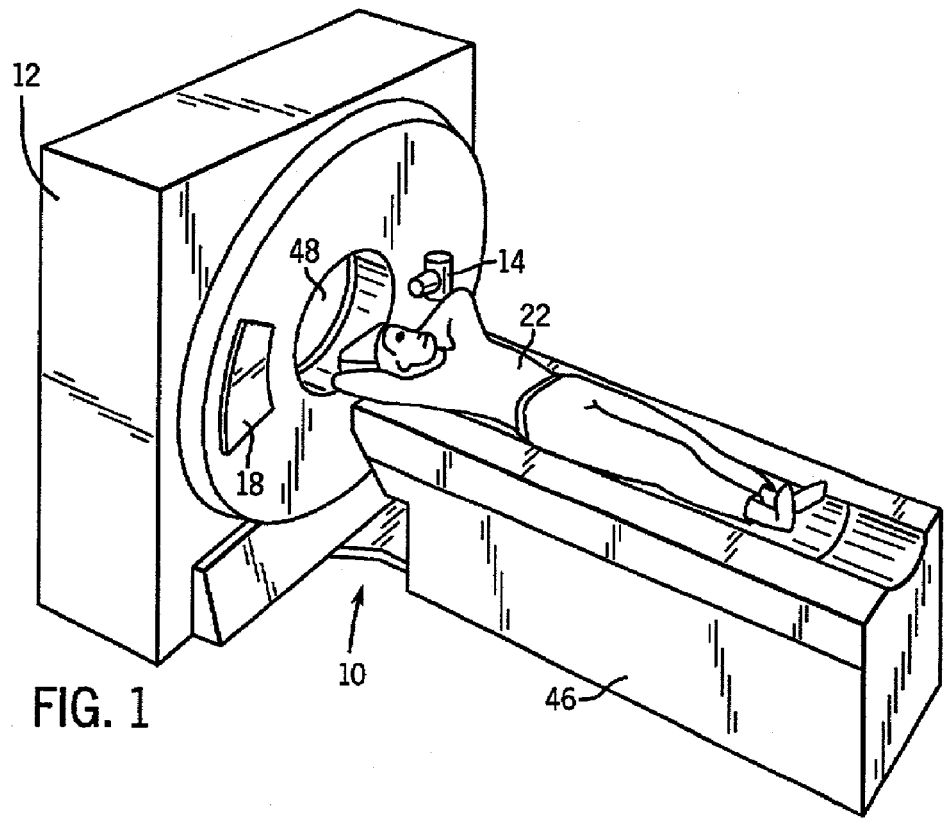
FIG. 1 is a pictorial view of a CT imaging system.
Figure 2:
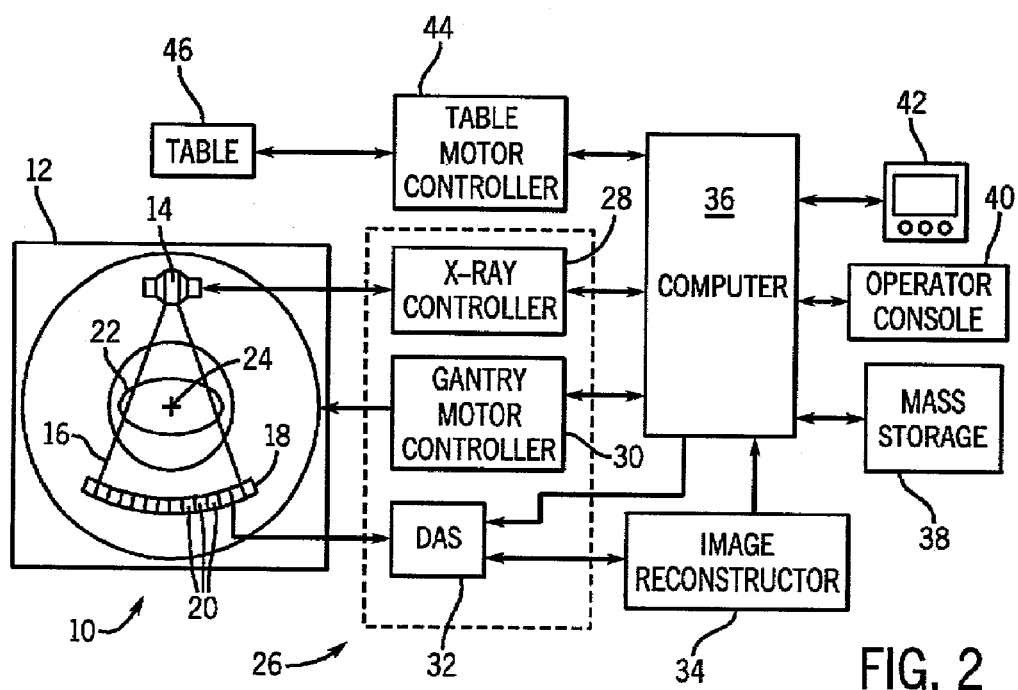
FIG. 2 is a block schematic diagram of the system illustrated in FIG. 1.

Referring to FIGS. 1 and 2, the present invention is applicable with a computed tomography (CT) system similar to that shown. That shown is representative of a "third generation" CT scanner but the present invention is also applicable with other CT systems. CT imaging system 10 includes a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical subject 22. Each detector 20 produces an electrical signal that represents the intensity of an impinging x-ray beam and hence the attenuated beam as it passes through the subject 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position subject 22 and gantry 12. Particularly, table 46 moves portions of subject 22 through a gantry opening 48.

Figure 3:
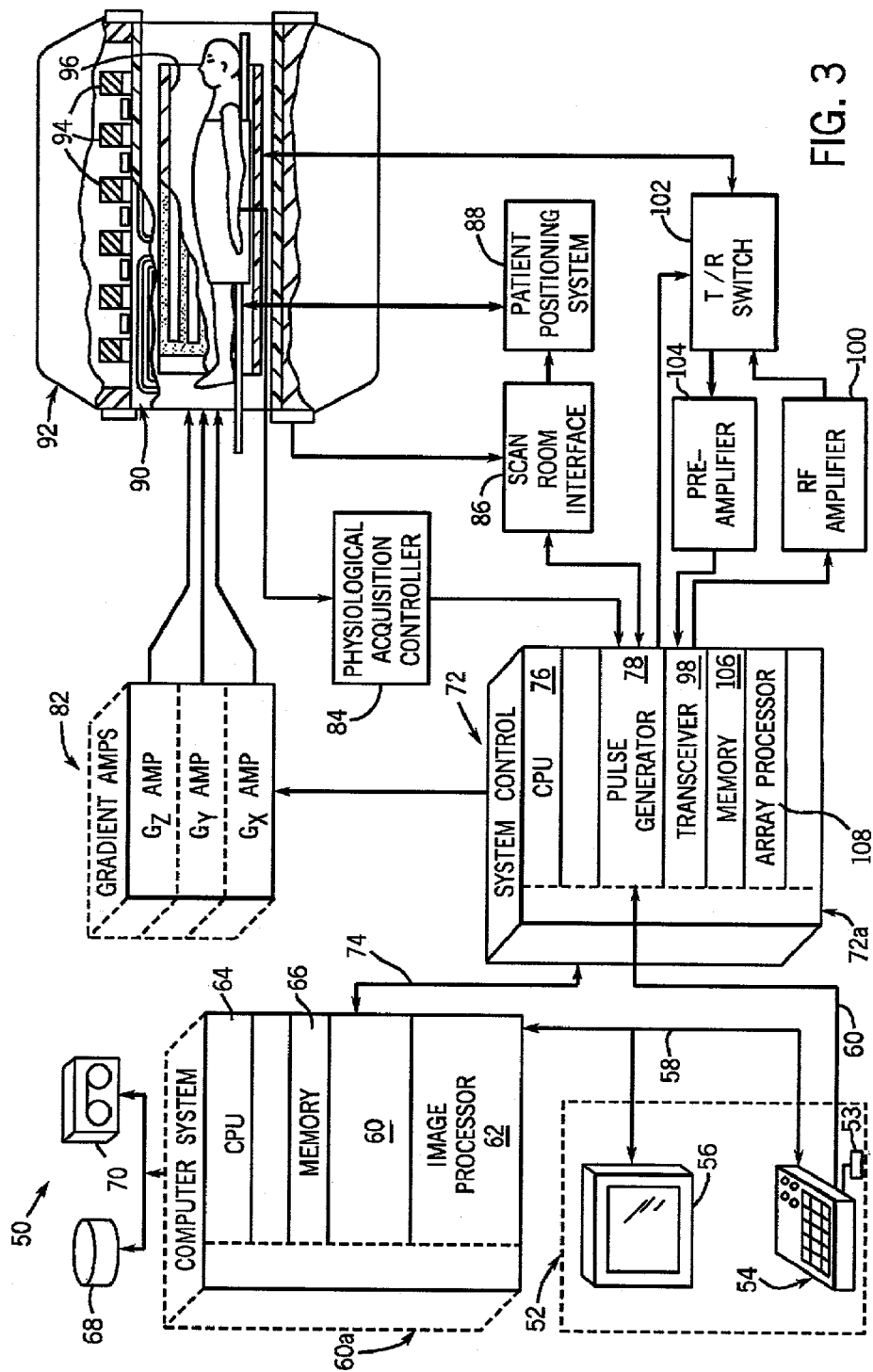
FIG. 3 is a schematic block diagram of an MR imaging system for use with the present invention.

Referring to FIG. 3, the major components of a preferred magnetic resonance imaging (MRI) system 50 incorporating the present invention are shown. The operation of the system is controlled from an operator console 52 which includes a keyboard or other input device 53, a control panel 54, and a display 56 or screen. The console 52 communicates through a link 58 with a separate computer system 60 that enables an operator to control the production and display of images on the screen 56. The computer system 60 includes a number of modules which communicate with each other through a backplane 60a. These include an image processor module 62, a CPU module 64 and a memory module 66, known in the art as a frame buffer for storing image data arrays. The computer system 60 is linked to disk storage 68 and tape drive 70 for storage of image data and programs, and communicates with a separate system control 72 through a high speed serial link 74. The input device 53 can include a mouse, joystick, keyboard, track ball, touch activated screen, light wand, voice control, or any similar or equivalent input device, and may be used for interactive geometry prescription.

The system control 72 includes a set of modules connected together by a backplane 72a. These include a CPU module 76 and a pulse generator module 78 which connects to the operator console 52 through a serial link 80. It is through link 80 that the system control 72 receives commands from the operator to indicate the scan sequence that is to be performed. The pulse generator module 78 operates the system components to carry out the desired scan sequence and produces data which indicates the timing, strength and shape of the RF pulses produced, and the timing and length of the data acquisition window. The pulse generator module 78 connects to a set of gradient amplifiers 82, to indicate the timing and shape of the gradient pulses that are produced during the scan. The pulse generator module 78 can also receive subject data from a physiological acquisition controller 84 that receives signals from a number of different sensors connected to the subject, such as ECG signals from electrodes attached to the subject. And finally, the pulse generator module 78 connects to a scan room interface circuit 86 which receives signals from various sensors associated with the condition of the subject and the magnet system. It is also through the scan room interface circuit 86 that a subject positioning system 88 receives commands to move the subject to the desired position for the scan.

The gradient waveforms produced by the pulse generator module 78 are applied to the gradient amplifier system 82 having $G_x$, $G_y$, and $G_z$ amplifiers. Each gradient amplifier excites a corresponding physical gradient coil in a gradient coil assembly generally designated 90 to produce the magnetic field gradients used for spatially encoding acquired signals. The gradient coil assembly 90 forms part of a magnet assembly 92 which includes a polarizing magnet 94 and a whole-body RF coil 96. A transceiver module 98 in the system control 72 produces pulses which are amplified by an RF amplifier 100 and coupled to the RF coil 96 by a transmit/receive switch 102. The resulting signals emitted by the excited nuclei in the subject may be sensed by the same RF coil 96 and coupled through the transmit/receive switch 102 to a preamplifier 104. The amplified MR signals are demodulated, filtered, and digitized in the receiver section of the transceiver 98. The transmit/receive switch 102 is controlled by a signal from the pulse generator module 78 to electrically connect the RF amplifier 100 to the coil 96 during the transmit mode and to connect the preamplifier 104 to the coil 96 during the receive mode. The transmit/receive switch 102 can also enable a separate RF coil (for example, a surface coil) to be used in either the transmit or receive mode.

The MR signals picked up by the RF coil 96 are digitized by the transceiver module 98 and transferred to a memory module 106 in the system control 72. A scan is complete when an array of raw k-space data has been acquired in the memory module 106. This raw k-space data is rearranged into separate k-space data arrays for each image to be reconstructed, and each of these is input to an array processor 108 which operates to Fourier transform the data into an array of image data. This image data is conveyed through the serial link 74 to the computer system 60 where it is stored in memory, such as disk storage 68. In response to commands received from the operator console 52, this image data may be archived in long term storage, such as on the tape drive 70, or it may be further processed by the image processor 62 and conveyed to the operator console 52 and presented on the display 56.

The present invention may be implemented with a CT system as well as an MR system such as those heretofore described with respect to FIGS. 1–3. Furthermore, the present invention is equivalently applicable with other diagnostic imaging modalities including, but not limited to, x-ray systems, PET systems, and ultrasound.

Figure 4:
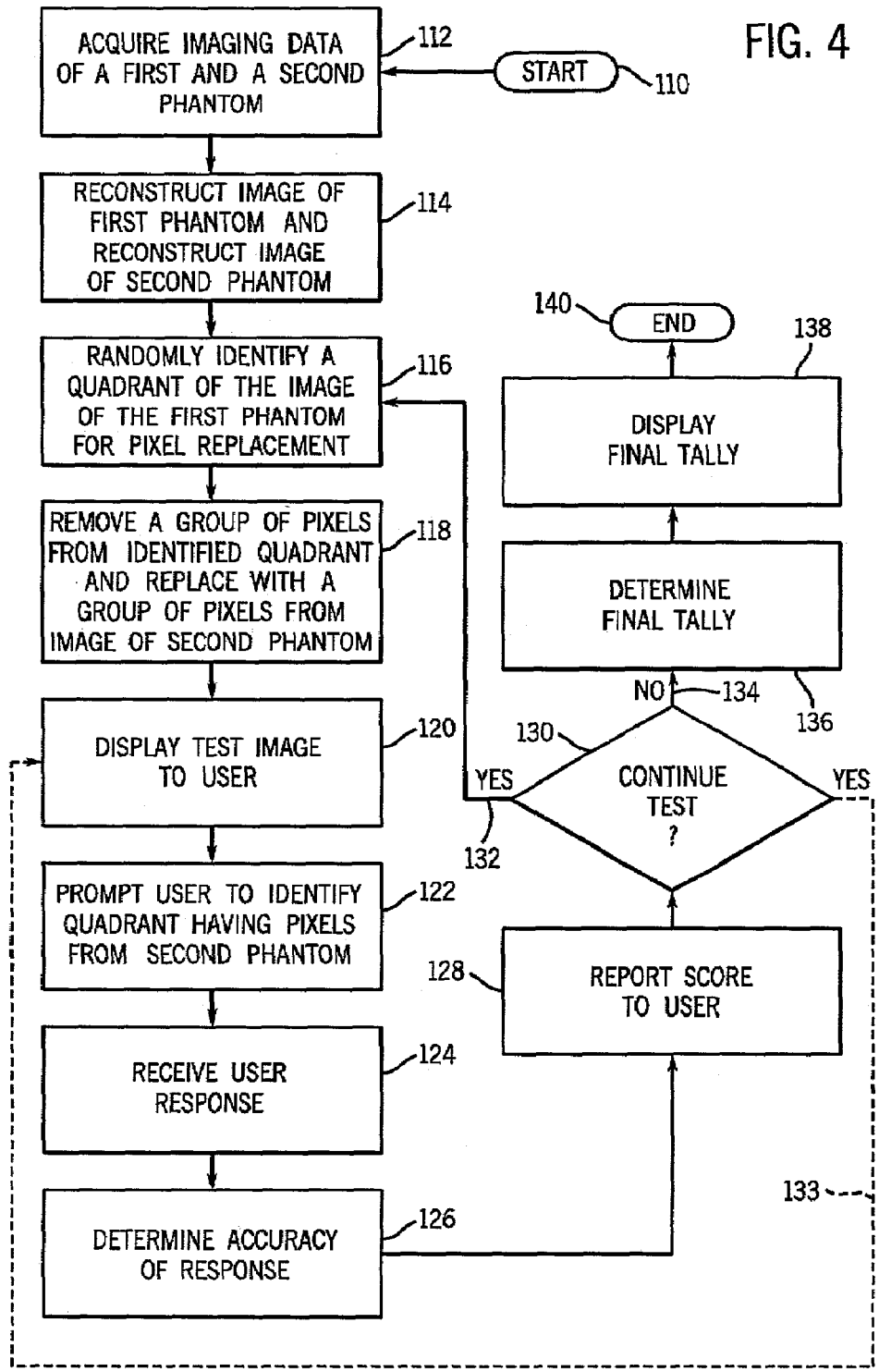
FIG. 4 is a flow chart setting forth the steps of detecting a low contrast object in a diagnostic image in accordance with the present invention.

Referring now to FIG. 4, the steps of a process for carrying out the present invention are set forth. FIG. 4 will be described with respect to a process which may be equivalently implemented as a method or a computer program. The process begins at 110 with the placement of a first phantom and a second phantom in a scanning bay such as that shown in FIGS. 1 and 3. The first phantom is characteristically defined as a uniform phantom having a generally uniform noise intensity whereas the second phantom is defined as one or more low contrast detectability (LCD) objects in a uniform field or an LCD phantom. Once the phantoms are properly positioned for data acquisition, imaging data of the phantoms is acquired at 112. Following the acquisition of imaging data 112, at least one image of the first phantom and at least one image of the second phantom are reconstructed at 114. At 116, a quadrant of the image of the first phantom is randomly selected for pixel replacement. At least one pixel, and preferably, a group of pixels, is then removed from the quadrant identified at 116 and replaced with at least one pixel from an image of the second phantom at 118. Preferably, the pixels removed from the first phantom should be replaced with an equal number and equally sized pixels from the second phantom.

Once the pixels of the second phantom are incorporated into the image of the first phantom, a test image is displayed to the user at 120. The test image is a composite of the first image having at least one pixel from the second image in a quadrant thereof. The user or observer is then prompted at 122 to identify the quadrant having the pixels from the second phantom. That is, the pixels of the second image correspond to imaging data of a low contrast object. Therefore, the pixels from the second phantom should be distinguishable when compared to the pixels of the first phantom.

The image of a round uniform phantom generally contains noise with a uniform intensity that may very slightly as a function of radial position. That is, the noise at any radial distance is generally similar, especially within 5 cm of the center. Thus, in a uniform phantom, it would be impossible to detect that a group of pixels was interchanged with another group of pixels as long as the pixels are located at 90° increments from the original position and are located at the same radial location and orientation from center. Pixels groups could be similarly moved between different images having the same noise characteristics. Thus, in a phantom containing a fixed low contrast feature, the pixels containing that feature could be randomly moved by a software tool from one location to another without the observer's knowledge.

Once the user is prompted to identify the quadrant having or corresponding to the LCD object, a user response identifying the quadrant is received at 124. A determination of the accuracy of the user response is then determined at 126. At 128, the accuracy score is reported to the user. The present invention contemplates a number of scoring values including a simple "true-false" score but other scoring values are contemplated and within the scope of the present invention.

Once the user receives the score, the user has the option to continue with the testing process at 130. If the user desires to continue with the test 130, 132, the process returns to step 116 with the random selection of a quadrant to which pixels of the second image are to be incorporated within a second image of the first phantom. As a result, there is only a 25% chance that the same quadrant as that previously selected will be randomly chosen for the second test image. Therefore, the user must determine in each image the presence of the LCD object rather than relying on the knowledge that the LCD object is in the same quadrant for each image. Alternately, the user may indicate desire to reselect the quadrant believed to be containing the LCD pixels 133. If the user elects not to continue with the test 130, 134, a final accuracy score tally is determined at 136. The final tally is indicative of the accuracy of all user responses for a particular test sequence. For example, accurate identification in nine of twelve images would result in an accuracy score of 75% being conveyed to the user at 138. Other messages could also be conveyed to the user including a "passed" or "failed" indicator. After the final tally is displayed to the user at 138, the process ends at 140. It will be apparent to those skilled in the art that the process could be repeated for various size LCD patterns and a set of ROC curves could be generated as a comprehensive assessment of the performance of the imaging system. Furthermore, the LCD objects could be randomly positioned within a matrix of many locations in the uniform phantom instead of in just one of four quadrant locations. The user would identify which locations are believed to contain the object so that a statistical score could be generated.

As heretofore described, the present invention is applicable across a number of imaging modalities and may be implemented with a single user rather than requiring one user to acquire the imaging data knowing where the LCD object is in the reconstructed images and while another user tries to ascertain the location of an LCD object within the images.

Accordingly, in accordance with one embodiment of the present invention, a method of testing the low contrast performance of an imaging system is provided. The method includes the steps of positioning a first phantom and a second phantom in a scanning bay and acquiring imaging data of the phantoms. The method further includes the step of reconstructing a set of images for each of the phantoms from the imaging data wherein each image has a number of pixels. At least one pixel from an image of the first phantom is then interchanged with at least one pixel from an image of the second phantom and thereafter a user is prompted to identify the at least one pixel interchanged into the image of the first phantom.

In accordance with another embodiment of the present invention, a computer readable storage medium having a computer program stored thereon for assisting a user in identifying a low contrast objects in an image is provided. The computer program represents a set of instructions that when executed by a computer causes the computer to access an image of a uniform phantom as well as access an image of an LCD phantom. The set of instructions then causes the computer to randomly remove the set of pixels of the image of the uniform phantom and replace with a set of pixels of the image of the LCD phantom. A test image is then reconstructed therefrom. The computer is then caused to display the test image and prompt the user to identify the set of pixels from the image of the LCD phantom within the test image.

In accordance with a further embodiment of the present invention, a diagnostic imaging system includes an imaging bay and a table configured to position a subject to be imaged in the imaging bay. The imaging system further includes a DAS configured to acquire imaging data of the subject as well as a computer programmed to acquire imaging data of a uniform phantom and an LCD phantom. The computer is also programmed to reconstruct an image of the uniform phantom from the imaging data wherein the uniform phantom has a generally uniform noise intensity. The computer is also programmed to reconstruct an image of the LCD phantom from the imaging data. A portion of the image of the LCD phantom is then incorporated into the image of the uniform phantom to form a test image. The computer is then programmed to display the test image to a user and prompt the user to identify the portion of the test image corresponding to the LCD phantom. A user response is then received and an accuracy of the user response is determined.

While the present invention has been described with respect to a method and apparatus of testing an imaging system, the present invention may be equivalently used as a training tool. That is, the present invention may be used to train radiologists in artifact detection. For example, lesions may be introduced into a set of images and then displayed to a student or trainee for evaluation.

The present invention has been described in terms of the preferred embodiment, and it is recognized that equivalents, alternative, and modifications, aside from those expressly stated, are possible and within the scope of the appending claims.

What is claimed is:

1. A method of testing the low contrast performance of an imaging system comprising the steps of:
   (A) positioning a first phantom and a second phantom in a scanning bay;
   (B) acquiring imaging data of the phantoms;
   (C) reconstructing a set of images for each of the phantoms from the imaging data, each image having a number of pixels;
   (D) interchanging at least one pixel from an image of the first phantom with at least one pixel from an image of the second phantom; and
   (E) prompting a user to identify the at least one pixel interchanged into the image of the first phantom.

2. The method of claim 1 further comprising the step of indicating to the user if the at least one pixel interchanged into the image of the first phantom was properly identified.

3. The method of claim 1 wherein the step of interchanging includes the step of randomly replacing at least one pixel from the image of the first phantom with at least one pixel from the image of the second phantom.

4. The method of claim 3 wherein the step of randomly replacing includes the step of removing at least one pixel from one quadrant of the image of the first phantom and incorporating at least one pixel of the image of the second phantom therein.

5. The method of claim 1 further comprising the step of repeating steps (D)–(E) for each image of the set of images.

6. The method of claim 5 further comprising the step of determining a total accuracy score corresponding to an accuracy in identifying the at least one pixel interchanged into the image of the first phantom for each of the set of images.

7. The method of claim 1 wherein the first phantom includes a spherical uniform phantom having a generally uniform noise intensity and wherein the second phantom includes a phantom with low contrast detectability (LCD) objects.

8. The method of claim 7 wherein the at least one pixel of the image of the second phantom interchanged into the image of the first phantom includes a group of pixels corresponding to an object with LCD.

9. A computer readable storage medium having a computer program stored thereon for assisting a user in identifying a low contrast object in an image and having a set of instructions that when executed by a computer causes the computer to:
   access an image of a uniform phantom;
   access an image of an LCD phantom;
   randomly remove a set of pixels of the image of the uniform phantom and replace with a set of pixels of the image of the LCD phantom;
   reconstruct a test image therefrom; and
   display the test image and prompt the user to identify the set of pixels from the image of the LCD phantom within the test image.

10. The computer readable storage medium of claim 9 wherein the set of instructions further causes the computer to:
    determine an accuracy of a user response identifying the set of pixels from the image of the LCD phantom within the test image; and
    convey the accuracy to the user.

11. The computer readable storage medium of claim 9 wherein the set of instructions further causes the computer to randomly remove the set of pixels from a quadrant of the image of the uniform phantom and incorporate the set of pixels of the image of the LCD phantom in the quadrant.

12. The computer readable storage medium of claim 11 wherein the set of instructions further causes the computer to prompt the user to identify the quadrant of the test image having the set of pixels of the image of the LCD phantom.

13. The computer readable storage medium of claim 9 wherein the set of instructions to access an image of a uniform phantom further includes instructions to cause the computer to select one image from a set of images of the uniform phantom stored on a database.

14. The computer readable storage medium of claim 13 wherein the set of instructions further causes the computer to reconstruct the set of images of the uniform phantom from imaging data acquired of the uniform phantom and store the set of images of the uniform phantom on the database.

15. The computer readable storage medium of claim 9 wherein the set of instructions to access an image of an LCD phantom further includes instructions to cause the computer to select one image from a set of images of the LCD phantom stored on a database.

16. The computer readable storage medium of claim 15 wherein the set of instructions further causes the computer to reconstruct the set of images of the LCD phantom from imaging data acquired of the LCD phantom and store the set of images of the LCD phantom on the database.

17. The computer readable storage medium of claim 9 wherein the set of instructions further causes the computer to randomly remove the set of pixels of the image of the uniform phantom from a region of the image of the uniform phantom having uniform noise intensity.

18. A diagnostic imaging system comprising:
an imaging bay;
a table configured to position a subject to be imaged in the imaging bay;
a DAS configured to acquire imaging data of the subject; and
a computer programmed to:
(A) acquire imaging data of uniform phantom and an LCD phantom;
(B) reconstruct an image of the uniform phantom from the imaging data, the uniform phantom having a generally uniform noise intensity;
(C) reconstruct an image of the LCD phantom from the imaging data;
(D) incorporate a portion of the image of the LCD phantom into the image of the uniform phantom and form a test image therefrom;
(E) display the test image to a user and prompt the user to identify the portion of the test image corresponding to the LCD phantom; and
(F) receive a user response and determine an accuracy score thereof.

19. The diagnostic imaging system of claim 18 wherein the computer is further programmed to convey the accuracy score to the user.

20. The diagnostic imaging system of claim 18 wherein the portion of the image of the LCD phantom includes a set of pixels corresponding to an LCD object.

21. The diagnostic imaging system of claim 18 wherein the computer is further programmed to reconstruct additional images of the uniform phantom and the LCD phantom and repeat acts (D)–(F) for each additional image of the uniform phantom and the LCD phantom.

22. The diagnostic imaging system of claim 21 wherein the computer is further programmed to determine and convey a total accuracy score for all user responses.

23. The diagnostic imaging system of claim 18 incorporated into at least one of an ultrasound system, an x-ray system, a CT system, and an MR system.

* * * * *